(12) United States Patent
Kerrish et al.

(10) Patent No.: US 7,723,310 B2
(45) Date of Patent: May 25, 2010

(54) LARGE DOSE RIBAVIRIN FORMULATIONS

(75) Inventors: Donald Joseph Kerrish, Baden, PA (US); Ravindra Dhanantwari, Economy, PA (US)

(73) Assignee: Three Rivers Pharmaceuticals, LLC, Cranberry Township, PA (US)

( * ) Notice: Subject to any disclaimer, the term of this patent is extended or adjusted under 35 U.S.C. 154(b) by 911 days.

(21) Appl. No.: 11/201,311

(22) Filed: Aug. 11, 2005

(65) Prior Publication Data

US 2006/0083785 A1 Apr. 20, 2006

Related U.S. Application Data

(60) Provisional application No. 60/619,013, filed on Oct. 18, 2004.

(51) Int. Cl.
*A61K 31/70* (2006.01)
*A61K 9/48* (2006.01)
*A61K 9/20* (2006.01)
*A01N 43/04* (2006.01)

(52) U.S. Cl. .................. 514/43; 424/451; 424/464

(58) Field of Classification Search .............. 514/43; 424/451, 464
See application file for complete search history.

(56) References Cited

U.S. PATENT DOCUMENTS 4,971,951 A * 11/1990 Garcia y Bellon et al. ...... 514/3
5,316,772 A * 5/1994 Jurgens et al. ............ 424/472
5,549,204 A    8/1996 Toren
6,337,090 B1   1/2002 Liebowitz et al.
6,472,373 B1  10/2002 Albrecht
6,720,000 B2   4/2004 Kerrish et al.
2001/0048988 A1 12/2001 Forte et al.
2003/0104050 A1  6/2003 Matharu et al.
2005/0019406 A1  1/2005 Kerrish et al.
2005/0281872 A1 12/2005 Summerville et al.
2006/0083785 A1  4/2006 Kerrish et al.

FOREIGN PATENT DOCUMENTS

AU   200116683 A1   4/2001
EP   1 005 868 A1   6/2000
WO   WO 99/33795 A1  7/1999
WO   WO 00/37097 A1  6/2000

OTHER PUBLICATIONS

VH Tam, et al., "Comparative Pharmacokinetic Analysis by Standard Two-Stage Versus Nonparametric Population Modeling" *Pharmacotherapy* 23(12): pp. 1545-1549 (2003).
MW Fried, et al., "Peginterferon Alfa-2a Plus Ribavirin for Chronic Hepatitis C Virus Infection" *New England J Med* 347(13): pp. 975-982 (2002).

(Continued)

*Primary Examiner*—Frederick Krass
*Assistant Examiner*—Benjamin Packard
(74) *Attorney, Agent, or Firm*—Arent Fox LLP

(57) ABSTRACT

The present invention is related to pharmaceutical dosage forms of ribavirin which are designed to increase patient compliance to a ribavirin therapy. Examples of such dosage forms include 400 mg to 600 mg tablets. These dosage forms are bioequivalent to multiple doses of tablets containing small amounts of ribavirin.

17 Claims, 1 Drawing Sheet

Mean Ribavirin Plasma Levels

OTHER PUBLICATIONS

N Kontorinis et al., "Outcome, tolerability and compliance of compassionate use interferon and ribavirin for hepatitis C infection in a shared care hospital clinic" *Internal Medicine Journal* 33: pp. 500-504 (2003).

BSE August-Forg et al., "Twenty-four vs. forty-eight weeks of re-therapy with interferon alpha 2b and ribavirin in interferon alpha monotherapy relapsers with chronic hepatitis C", *Swiss Medicine Weekly* vol. 133: pp. 455-460 (2003).

Brownlee, "Adding that 'spoonful of sugar'—more", Modern Drug Discovery (2002) vol. 5, No. 5, pp. 34-36, posted online at http://pubs.acs.org/subscribe/journals/mdd/v05/i05/htm/05brown.html.

Guidotti, "Laxative components of a generic drug", The Lancet (1996) vol. 347, p. 621.

Carmen Mak et al, "Compliance as an Explanatory Variable in Hepatitis C", Drug Information Journal (2001), vol. 35, No. pp. 1351-1361.

McHutchinson et al, "Adherence to Combination Therapy Enhances Sustained Response in Genotype-1-Infected Patients with Chronic Hepatitis C" Gastroenterology (2002), vol. 123, pp. 1061-1069.

Pol et al., "Optimizing Treatment Outcomes in Chronic Hepatitis C: management of non-response", (2006), pp. 955-970.

Morisco et al., Tomato-based Functional Food as Interferon Adjuvant in HCV Eradication Therapy, (2004), vol. 38, pp. 118-120.

Raptopoulou et al., The effect of adherence to therapy on sustained response in daily or three times a week interferon alpha-2b plus ribavirin treatment of naïve and nonresponder chronic hepatitis C patients, (2005), pp. 91-95.

Darling et al., "Optimizing Treatment Regimens in Hepatitis C", (Clin Liver Dis 10 (2006), pp. 835-850.

Carmen Mak, "Compliance as an Explanatory Variable in Hepatitis-C", posted online at http://findarticles.com/p/aricles/mi_qa3899/is_200110/ai_n8956250/print.

Kraus et al., Paroxetine for the treatment of interferon-x-induced depression in chronic hepatitis C (2002), pp. 1091-1099.

Dieterich et al., Once-Weekly Epoetin Alfa Improves Anemia and Facilitates Maintenance of Ribavirin Dosing in Hepatitis C Virus-Infected Patients Receiving Ribavirin Plus Interferon Alfa, (2003), vol. 98, No. 11, pp. 2491-2499.

Correspondence from Jay P. Lessler of Darby & Darby dated Feb. 1, 2010.

* cited by examiner

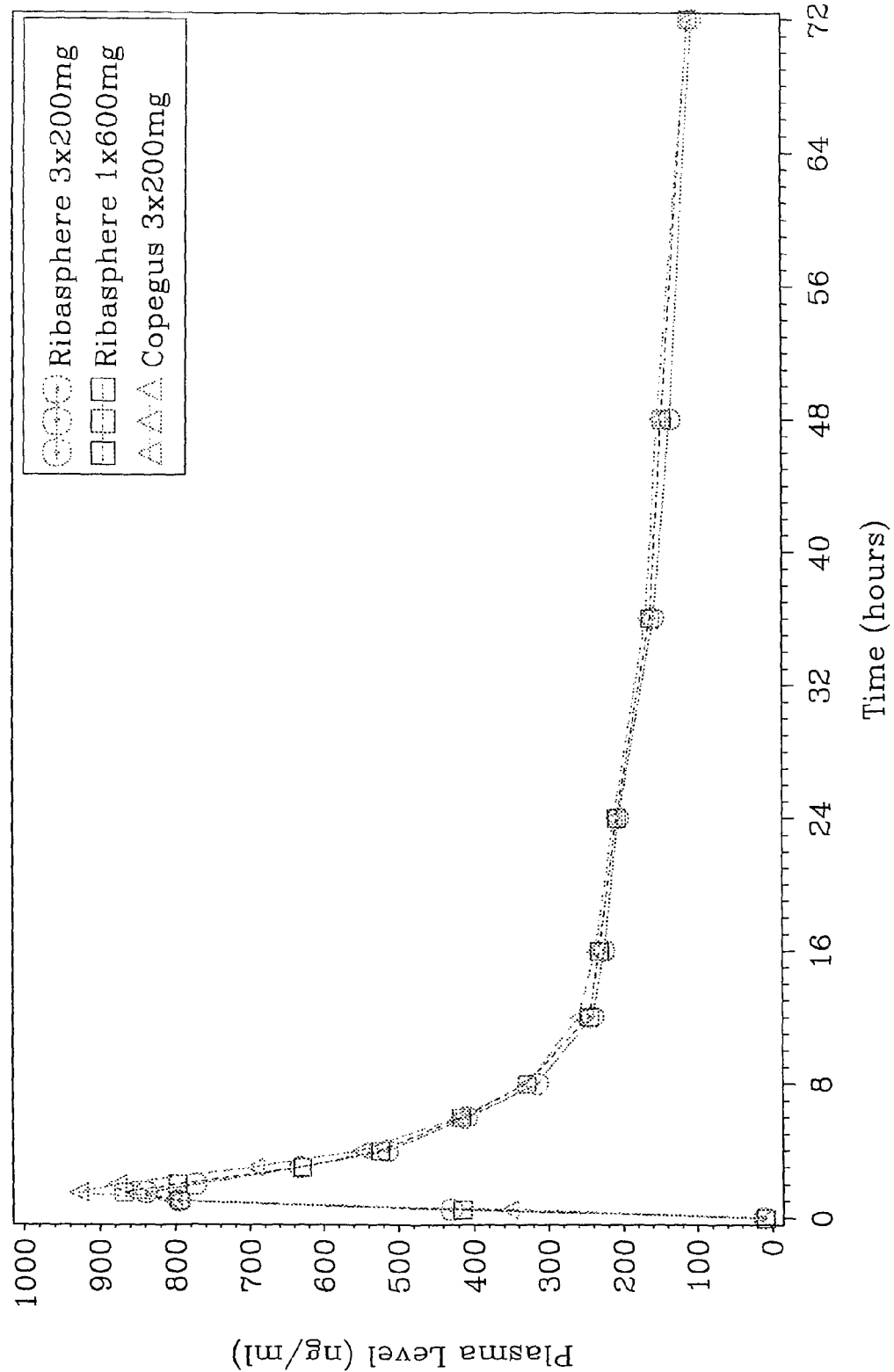
Figure 1: Mean Ribavirin Plasma Levels

LARGE DOSE RIBAVIRIN FORMULATIONS

CROSS-REFERENCE TO RELATED APPLICATIONS

This application claims priority to U.S. provisional application No. 60/619,013, filed Oct. 18, 2004, the contents of which are hereby incorporated in their entirety by reference.

BACKGROUND OF THE INVENTION

1. Field of the Invention

The invention is generally directed to large dosage formulations of ribavirin.

2. Background of the Invention

Ribavirin (1-β-D-ribofuranosyl-1H-1,2,4-triazole-3-carbamide) is a broad-spectrum antiviral nucleoside analog. It is available as a capsule and tablet in both the brand and generic form in 200 mg strength. The Food and Drug Administration has approved ribavirin in combination with interferon alfa-2*a* or interferon alfa-2*b* for the treatment of hepatitis-C. Over 170 million people worldwide are chronically infected with the hepatitis-C virus (HCV). Ribavirin is available as a 200 mg tablet by Roche Laboratories under the brand COPEGUS™ and as a 200 mg capsule by Schering-Plough under the brand REBETOL™.

The most common doses prescribed for patients are 800 mg, 1000 mg, and 1200 mg per day in divided doses for both the capsule and tablet dosage forms. These dosing regimens have the patient taking up to 6 capsules or tablets per day. Ribavirin is not often given by itself; it is generally a component of a multi-drug regimen ("drug cocktail"). Therefore patients taking ribavirin have to take a large number of drugs, not in the least of which is 4 to 6 capsules or tablets of ribavirin. Not surprisingly, lack of patient compliance is a significant issue.

HCV has about a 50 percent cure rate depending upon a patient's genotype. Everything must be done to ensure patient compliance to the therapy that lasts 6 to 12 months. If dosing is more convenient for the patient, then it follows that the patient will more likely comply with the dosing regimen for the duration of therapy, which has been proven to improve patient outcomes.

Therefore, there exists a long-felt need to make the dosing of ribavirin more convenient for the patient and increase patient compliance.

From a convenience standpoint, one logical approach to the formulator would be to formulate a modified or sustained release form of ribavirin, which would result in fewer capsules or tablets taken daily. However, in the case of ribavirin, such an approach would not be successful. The pharmacokinetics of ribavirin are controlled by the rate of elimination, not absorption. Therefore, modifying the rate of release or absorption of ribavirin would not likely affect the efficacy of ribavirin. In other words, sustained release formulations of ribavirin are likely not a solution in this instance.

The present inventors have concluded that in the case of ribavirin, the optimal dosage regimen is two times a day. The inventors then strove to formulate dosage forms with a twice-a-day dosing regimen which would increase patient compliance while maintaining bioactivity similar to lower (e.g., 200 mg) dose formulations.

SUMMARY OF THE INVENTION

One aspect of the present invention is directed to an oral dosage form of ribavirin, preferably a capsule, tablet or caplet, in 400 mg to 600 mg dosage strengths.

Another aspect of the present invention is directed to dosage forms of ribavirin that increase patient compliance.

Another aspect of the invention is directed to dosage forms of ribavirin that satisfy a long-felt need in the market for ribavirin dosage forms.

Another aspect of the invention is directed to dosage forms of ribavirin comprising high amounts of ribavirin, relative to commercially available formulations, which have similar bioactivities to the commercially available formulations.

A further aspect of the invention is directed to a dosage form comprising 400 mg of ribavirin.

A further aspect of the invention is directed to a dosage form comprising 600 mg of ribavirin.

Another aspect of the invention is directed to dosage forms of ribavirin in unit dose packaging, such as blister packaging.

Other aspects, features, and advantages of the invention will become apparent from the following detailed description and figure.

BRIEF DESCRIPTION OF THE FIGURE

FIG. 1 shows mean in vivo ribavirin plasma levels of three formulations in a bioavailability study of 36 subjects. COPEGUS™ 3×200 mg means that the brand name ribavirin product was given in a dosage of three 200 mg tablets. RIBASPHERE™ 3×200 mg means that the generic ribavirin product was given in a dosage of three 200 mg tablets. RIBASPHERE™ 1×600 mg means that a ribavirin product according to the invention was given at a dosage of one 600 mg tablet.

DETAILED DESCRIPTION OF THE INVENTION

In accordance with the present invention, the term "dosage form" includes capsules and tablets, and the term "tablet" includes both tablets and caplets. The dosage form of the invention is preferably a tablet, and more preferably a caplet.

The present application describes the development of dosage forms of ribavirin in 400 mg to 600 mg dosage strengths. In order to test bioequivalency, subjects were dosed with 600 mg tablets. A corresponding number of COPEGUS™ and generic 200 mg tablets were used as a comparison. FIG. 1 shows that the in vivo dissolution profile of a 600 mg tablet according to the present invention is similar to the dissolution profile of three 200 mg COPEGUS™ tablets. In other words, the higher strength tablets according to the present invention are bioequivalent to the brand name product. Further, the preferred caplet shape makes it easier for the patient to swallow and the tablets are acceptable as not being too large in size.

The patient now only has to take one tablet twice a day instead of 2 or 3 tablets twice a day. This new, more convenient dose keeps patients more compliant to their drug regimen, which improves outcomes. To this point, no drug manufacturer has manufactured a large dosage form of ribavirin. There is a clear and long-felt need in the industry for such a product.

The dosage forms of the present invention can be made of the same general ingredients (e.g., binders, fillers, disintegrants, lubricants and the like) and in the same manner as commercially available ribavirin tablets. In one embodiment of the present invention, a tablet comprises one or more of the following inactive ingredients: microcrystalline cellulose; lactose; crosscarmellose sodium; Povidone; and magnesium stearate. In another embodiment of the present invention, the tablet is coated and the coating preferably comprises: Opandry II Blue (which in turn comprises polyvinyl alcohol-part hydrolyzed, titanium dioxide, macrogel/PEG 3350, talc, and FD&C blue #2/indigo carmine aluminum lake); and carnauba wax.

One example of the formulation of a 400 mg ribavirin tablet in accordance with the present invention is shown in Table I:

TABLE I

| Component | Weight/tablet (mg) | Ingredient |
|---|---|---|
| Active | 400.0 | Ribavirin |
| Binder/disintegrant | 84.4 | Microcrystalline cellulose |
| Filler | 30.0 | Lactose monohydrate |
| Disintegrant | 25.4 | Crosscarmellose sodium |
| Binder | 6.0 | Povidone |
| Lubricant | 4.2 | Magnesium stearate |
| Water | (removed during drying) | Purified water |

One example of the formulation of a 600 mg ribavirin tablet in accordance with the present invention is shown in Table II:

TABLE II

| Component | Weight/tablet (mg) | Ingredient |
|---|---|---|
| Active | 600.0 | Ribavirin |
| Binder/disintegrant | 126.6 | Microcrystalline cellulose |
| Filler | 45.0 | Lactose monohydrate |
| Disintegrant | 38.1 | Crosscarmellose sodium |
| Binder | 9.0 | Povidone |
| Lubricant | 6.3 | Magnesium stearate |
| Water | (removed during drying) | Purified water |

One embodiment of a 400 mg tablet according to the present invention has hardness of from about 10.27 kp to about 12.88 kp, preferably 11.18 kp. Another embodiment of a 400 mg tablet according to the present invention has a tablet weight of from about 0.5470 g to about 0.5535 g, preferably 0.5494 g. Another embodiment of a 400 mg tablet according to the present invention has a tablet thickness of from about 4.86 mm to about 4.91 mm, preferably 4.89 mm. Another embodiment of a 400 mg tablet according to the present invention has a tablet friability of from about 0.23% to about 0.26%, preferably 0.25%. Another embodiment of a 400 mg tablet according to the present invention has a compression force of from about 13.5 kN to about 16.6 kN, preferably 14.9 kN.

One embodiment of a 600 mg tablet according to the present invention has hardness of from about 10.64 kp to about 12.58 kp, preferably 11.60 kp. Another embodiment of a 600 mg tablet according to the present invention has a tablet weight of from about 0.8174 g to about 0.8357 g, preferably 0.8272 g. Another embodiment of a 600 mg tablet according to the present invention has a tablet thickness of from about 6.38 mm to about 6.41 mm, preferably 6.39 mm. Another embodiment of a 600 mg tablet according to the present invention has a tablet friability of from about 0.23% to about 0.33%, preferably 0.29%. Another embodiment of a 600 mg tablet according to the present invention has a compression force of from about 12.2 kN to about 14.2 kN, preferably 13.1 kN.

Compression and film coating of the tablets according to the present invention may be accomplished by standard industry means. For example, tablets may be compressed using a 16-station Manesty Beta press using capsule shaped tooling. The tablets may be film coated using a 24-inch Accela Cota pan equipped with 2 spray guns with a target air flow of about 300 cfm and an exhaust temperature of between about 50° C. to 55° C. The pan speed and the target spray rate can be adjusted to suit the particular tablet being coated. As indicated previously, in one embodiment, Opandry II Blue coating is used. Any suitable coating can be used in accordance with the present invention.

The tablets according to the present invention may be of any color, preferably blue, more preferably light-blue, medium blue, or dark blue. The tablets can also be of any shape, preferably flat and oval-shaped. The tablets may be dispensed in any form including blister packs and HDPE bottles, which may or may not include child-resistant closures with induction seals. Any number of tablets may be included in a unit dose package, such as a blister pack, including 2, 4, 6, 8, 10, 12, 16, 20, 24, 48 or 56.

EXAMPLE 1

A Comparative Bioavailability Study of Ribavirin Tablets Under Fasting Conditions Ribavirin plasma levels under fasting conditions, produced after administration of (a) three Ribasphere® 200 mg tablets and (b) one Ribasphere® 600 mg tablet were compared with those produced after administration of three Copegus® 200 mg tablets.

The 200 mg and 600 mg Ribasphere® tablets are manufactured by Three Rivers Pharmaceuticals, LLC; ribavirin tablets. The Copegus® 200 mg tablets were manufactured by Roche®.

The study was administered and coordinated by Bioanalytical Systems, Inc. (BASi), Clinical Research Unit (CRU), Baltimore, Md. The clinical portion of the study was conducted by Gateway Medical Research, Inc. The laboratory analysis of plasma samples and statistical analysis of the concentration-time data was conducted at BASi CRU. Forty-one healthy female subjects were enrolled in this three-treatment crossover study. Blood samples from all subjects who completed the study were analyzed. The subjects received a single oral dose of ribavirin 600 mg on three occasions separated by a washout period of three weeks. Blood samples were obtained at 15 time points from predose (0-hour) until 72 hours post-dose. The plasma samples were analyzed by a specific validated LC/MS/MS method to determine ribavirin concentrations.

The ribavirin concentrations were used to calculate the area under the concentration-time curve to the last non-zero time point ($AUC_{0-T}$), elimination rate constant ($K_{el}$), half-life ($T_{1/2}$) and AUC 0-Infinity ($AUC_{0-Inf}$). The actual times of sample collections were used in the calculations. The maximum drug concentration ($C_{max}$) and the time to maximum drug concentration ($T_{max}$) were also reported. The arithmetic mean and standard deviation were calculated for each parameter and for the ribavirin concentrations at each time point. The geometric means were calculated for $AUC_{0-T}$, $AUC_{0-Inf}$ and $C_{max}$. All parameters were analyzed by an analysis of variance (ANOVA) using the general linear model (GLM). The ANOVA included effects for sequence of drug treatment, subject nested within sequence, period and drug treatment in the statistical model. The F-test was employed to determine the statistical significance of each effect in the model. The sequence effect was tested using the subject (sequence) mean square as the error term ($\alpha=0.10$), while the other effects were tested against the residual error ($\alpha=0.05$). The power of the study to detect a 20% difference in parameter means as statistically significant under a 2-tailed test at the 5% level of the t-distribution was calculated for each pharmacokinetic metric.

The test and reference means (and geometric means), and the ratios of means, test/reference, were reported using the least squares means from the ANOVA. An assessment of bioequivalence was conducted for the test versus reference product comparison of AUC and $C_{max}$ after log transformation using 90% confidence intervals for the differences in treatment means. These were transformed into 90% confidence intervals for the ratios of the means (test/reference) by exponentiation. The products were considered bioequivalent if the 90% confidence intervals about the ratios of means for AUC and $C_{max}$ were contained within the limits 0.80 to 1.25.

Of the 41 subjects enrolled into the study, 36 subjects completed all study periods. The plasma samples were analyzed for all completed subjects. Several of the subjects experienced at least one adverse event. Ribavirin was measured in the predose sample of period I for one subject, in the predose sample of period II for nine subjects, and in the predose sample of period III for 21 subjects. The predose concentration detected was less than 5% of the individual $C_{max}$ value for all but four subjects.

The sampling schedule for ribavirin proved to be suitable for estimation of $T_{max}$ in this bioavailability study. The first post-dose sample was not the maximum observed concentration after 94 of the 96 doses. Two post-dose samples were obtained before the average time of the maximum concentration.

The sampling schedule was truncated at 72 hours post-dose for this long half-life drug, eighty percent of $AUC_{0-inf}$ was not typically measured by $AUC_{0-T}$. Therefore, in the results that follow, emphasis should be placed on $AUC_{0-T}$, since $AUC_{0-Inf}$ was not generally well estimated.

There were no statistically significant ($\alpha=0.05$) differences between the formulations for $AUC_{0-T}$ or $C_{max}$, while there was a statistically significant formulation difference observed for $AUC_{0-Inf}$. There were no statistically significant sequence effects ($\alpha=0.10$) for any AUC or $C_{max}$ parameter, and there was no statistically significant period effects ($\alpha=0.05$) for $C_{max}$.

The results show that three ribavirin Ribasphere® 200 mg tablets is bioequivalent to three Copegus® 200 mg tablets when both were administered under fasting conditions. Similarly, the ribavirin Ribasphere® 600 mg is bioequivalent to three ribavirin Copegus® 200 mg tablets when administered under fasting conditions. For $AUC_{0-T}$, $AUC_{0-Inf}$ and $C_{max}$, the 90% confidence intervals were within the 0.80 to 1.25 bioequivalence limits for both comparisons.

TABLE III

| Ribavirin (n-32) | Ratio of Means (test/reference) | 90% Confidence Interval |
|---|---|---|
| Ribasphere ® 3 × 200 mg vs. Copegus ® 3 × 200 mg | | |
| $AUC_{0-T}$ | 0.95 | 0.89; 1.00 |
| $AUC_{0-Inf}$ | 0.92 | 0.87; 0.97 |
| $C_{max}$ | 0.96 | 0.89; 1.03 |
| Ribasphere ® 1 × 600 mg vs. Copegus ® 3 × 200 mg | | |
| $AUC_{0-T}$ | 0.98 | 0.92; 1.04 |
| $AUC_{0-Inf}$ | 1.01 | 0.96; 1.07 |
| $C_{max}$ | 0.97 | 0.90; 1.05 |

Based on least squares after logarithmic transformation of the data

TABLE IV

RIBAVIRIN PLASMA CONCENTRATIONS (ng/ml)

| Time (Hours) | Test1: Ribasphere 3 × 200 mg | | | Test 2: Ribasphere 1 × 600 mg | | | Ref: Copegus 3 × 200 mg | | | Ratio Test1/Test2 | Ratio Test/Ref | Ratio Test2/Ref | Significance |
|---|---|---|---|---|---|---|---|---|---|---|---|---|---|
| | N | Mean | ±Std Dev | N | Mean | ±Std Dev | N | Mean | ±Std Dev | | | | |
| 0 | 32 | 9.319 | ±15.54 | 32 | 7.472 | ±13.36 | 32 | 8.713 | ±16.63 | 1.25 | 1.07 | 0.86 | |
| 0.5 | 32 | 435.0 | ±231.6 | 32 | 425.0 | ±255.1 | 32 | 348.5 | ±198.7 | 1.02 | 1.25 | 1.22 | N.S. |
| 1 | 32 | 811.5 | ±312.7 | 32 | 806.9 | ±267.8 | 32 | 825.0 | ±328.2 | 1.01 | 0.98 | 0.98 | N.S. |
| 1.5 | 32 | 859.2 | ±274.8 | 32 | 889.3 | ±317.9 | 32 | 965.6 | ±401.5 | 0.97 | 0.89 | 0.92 | N.S. |
| 2 | 32 | 794.5 | ±302.5 | 32 | 817.0 | ±272.7 | 32 | 907.2 | ±390.6 | 0.97 | 0.88 | 0.90 | N.S. |
| 3 | 32 | 648.3 | ±274.8 | 32 | 642.5 | ±221.2 | 32 | 706.0 | ±321.4 | 1.01 | 0.92 | 0.91 | N.S. |
| 4 | 32 | 528.8 | ±186.5 | 32 | 533.0 | ±169.7 | 32 | 552.7 | ±223.4 | 0.99 | 0.96 | 0.96 | N.S. |
| 6 | 32 | 419.5 | ±141.4 | 32 | 425.3 | ±151.1 | 32 | 422.1 | ±160.3 | 0.99 | 0.99 | 1.01 | N.S. |
| 8 | 32 | 320.1 | ±89.66 | 32 | 340.8 | ±117.8 | 32 | 330.9 | ±105.1 | 0.94 | 0.97 | 1.03 | N.S. |
| 12 | 32 | 246.5 | ±75.29 | 32 | 251.2 | ±81.48 | 32 | 260.2 | ±92.76 | 0.98 | 0.95 | 0.97 | N.S. |
| 16 | 32 | 230.4 | ±77.53 | 32 | 234.2 | ±68.48 | 32 | 240.6 | ±78.96 | 0.98 | 0.9'6 | 0.97 | N.S. |
| 24 | 32 | 211.2 | ±61.13 | 32 | 212.4 | ±70.36 | 32 | 214.9 | ±70.82 | 0.99 | 0.98 | 0.99 | N.S. |
| 36 | 31 | 158.6 | ±55.79 | 32 | 163.1 | ±55.60 | 30 | 171.4 | ±54.10 | 0.97 | 0.92 | 0.95 | N.S. |
| 48 | 31 | 136.0 | ±44.73 | 32 | 146.6 | ±42.12 | 32 | 152.7 | ±53.24 | 0.93 | 0.89+ | 0.96 | p < 0.05 |
| 72 | 32 | 106.0 | ±43.65 | 32 | 110.5 | ±35.09 | 32 | 111.4 | ±37.46 | 0.96 | 0.95 | 0.99 | N.S. |

TABLE V

PHARMACOKINETIC PARAMETERS FOR PLASMA RIBAVIRIN

| Parameter | N | Test1: Ribasphere 3 × 200 mg Mean ± Std Dev | N | Test2: Ribasphere 1 × 600 mg Mean ± Std Dev | N | Ref: Copegus 3 × 200 mg Mean ± Std Dev | Ratio Test1/Test2 | Ratio Test1/Ref | Ratio Test2/Ref |
|---|---|---|---|---|---|---|---|---|---|
| Ln $AUC_{0-T}$ Geometric Mean | 32 | 9.5776 ± 0.2769 14438 | 32 | 9.6097 ± 0.2683 14909 | 32 | 9.6302 ± 0.3008 15218 | 0.97 | 0.95 | 0.98 |
| Ln $AUC_{0-Inf}$ Geometric Mean | 32 | 9.9712 ± 0.3326 21401 | 31 | 10.0599 ± 0.3161 23387 | 30 | 10.0579 ± 0.3264 23339 | 0.92 | 0.92 | 1.00 |
| Ln $C_{max}$ Geometric Mean | 32 | 6.8292 ± 0.3181 924.4 | 32 | 6.8435 ± 0.2937 937.8 | 32 | 6.8703 ± 0.3793 963.2 | 0.99 | 0.96 | 0.97 |
| $AUC_{0-T}$ (ng · h/ml) | 32 | 15002 ± 4413 | 32 | 15447 ± 4288 | 32 | 15902 ± 4864 | 0.97 | 0.94 | 0.97 |
| $AUC_{0-Inf}$ (ng · h/ml) | 32 | 22645 ± 8290 | 31 | 24570 ± 8091 | 30 | 24576 ± 8255 | 0.92 | 0.92 | 1.00 |
| $C_{max}$ (ng/ml) | 32 | 971.1 ± 314.4 | 32 | 979.9 ± 315.9 | 32 | 1033 ± 402.6 | 0.99 | 0.94 | 0.95 |
| $T_{max}$ (h) | 32 | 1.501 ± 0.5680 | 32 | 1.455 ± 0.5605 | 32 | 1.517 ± 0.5301 | 1.03 | 0.99 | 0.96 |
| $K_{el}$ (1/h) | 32 | 0.01531 ± 0.003645 | 31 | 0.01407 ± 0.003963 | 30 | 0.01484 ± 0.003230 | 1.09 | 1.03 | 0.95 |
| $T_{1/2}$ (h) | 32 | 47.69 ± 10.71 | 31 | 53.61 ± 16.65 | 30 | 49.22 ± 12.41 | 0.89 | 0.97 | 1.09 |

TABLE VI

PHARMACOKINETIC PARAMETERS FOR PLASMA RIBAVIRIN

| Parameter | Test 1 Ribasphere 3 × 200 mg | Test 2 Ribasphere 1 × 600 mg | Reference Copegus 3 × 200 mg | Ratio Test1/Test2 | Ratio Test1/Ref | Ratio Test2/Ref | Significance |
|---|---|---|---|---|---|---|---|
| Ln $AUC_{0-T}$ Geometric Mean | 9.5829 ± 0.02500 (14515) | 9.6160 ± 0.02502 (15003) | 9.6380 ± 0.02497 (15337) | 0.97 | 0.95 | 0.98 | N.S. |
| Ln $AUC_{0-Inf}$ Geometric Mean | 9.9716 ± 0.02232 (21410) | 10.0689 ± 0.02286 (23597) | 10.0594 ± 0.02324 (23374) | 0.91+ | 0.92+ | 1.01 | p < 0.05 |
| Ln $C_{max}$ Geometric Mean | 6.8316 ± 0.03122 (926.7) | 6.8451 ± 0.03125 (939.2) | 6.8737 ± 0.03119 (966.5) | 0.99 | 0.96 | 0.97 | N.S. |
| $AUC_{0-T}$ (ng · h/ml) | 15108 ± 414.3 | 15566 ± 414.7 | 16051 t± 413.9 | 0.97 | 0.94 | 0.97 | N.S. |
| $AUC_{0-Inf}$ (ng · h/ml) | 22722 ± 625.5 | 24820 ± 640.9 | 24687 ± 651.4 | 0.92 | 0.92 | 1.01 | p < 0.05 |
| $C_{max}$ (ng/ml) | 974.6 ± 34.31 | 983.3 ± 34.34 | 1038 ± 34.28 | 0.99 | 0.94 | 0.95 | N.S. |
| $T_{max}$ (h) | 1.487 ± 0.09425 | 1.457 ± 0.09435 | 1.511 ± 0.09416 | 1.02 | 0.98 | 0.96 | N.S. |
| $K_{el}$ (1/h) | 0.01542 ± 0.000410 | 0.01393 ± 0.000420 | 0.01474 ± 0.000427 | 1.11+ | 1.05 | 0.95 | p < 0.05 |
| $T_{1/2}$ (h) | 47.29 ± 1.639 | 54.27 ± 1.679 | 49.74 ± 1.707 | 0.87+ | 0.95 | 1.09 | p < 0.05 |

TABLE VII

PHARMACOKINETIC PARAMETERS FOR PLASMA RIBAVIRIN

| Contrast of Means | Measured Parameter | Ratio (Test/Ref) | Study Power | Intrasubject C.V. (%) | 90% Confidence Interval |
|---|---|---|---|---|---|
| Ribasphere 3 × 200 mg vs. Ribasphere 1 × 600 mg | Ln $AUC_{0-T}$ | 0.97 | >0.99 | 14.1 | [0.91; 1.03] |
| | Ln $AUC_{0-Inf}$ | 0.91 | >0.99 | 12.6 | [0.86; 0.96] |
| | Ln $C_{max}$ | 0.99 | >0.99 | 17.7 | [0.92; 1.06] |
| | $AUC_{0-T}$ (ng · h/ml) | 0.97 | >0.99 | 15.1 | [0.91; 1.03] |
| | $AUC_{0-Inf}$ (ng · h/ml) | 0.92 | >0.99 | 14.7 | [0.86; 0.98] |
| | $C_{max}$ (ng/ml) | 0.99 | 0.98 | 19.4 | [0.91; 1.07] |
| Ribasphere 3 × 200 mg vs. Copegus 3 × 200 mg | Ln $AUC_{0-T}$ | 0.95 | >0.99 | 14.1 | [0.89; 1.00] |
| | Ln $AUC_{0-Inf}$ | 0.92 | >0.99 | 12.6 | [0.87; 0.97] |
| | Ln $C_{max}$ | 0.96 | >0.99 | 17.7 | [0.89; 1.03] |
| | $AUC_{0-T}$ (ng · h/ml) | 0.94 | >0.99 | 15.1 | [0.88; 1.00] |
| | $AUC_{0-Inf}$ (ng · h/ml) | 0.92 | >0.99 | 14.7 | [0.86; 0.98] |
| | $C_{max}$ (ng/ml) | 0.94 | 0.99 | 19.4 | [0.86; 1.02] |
| Ribasphere 1 × 600 mg vs. Copegus 3 × 200 mg | Ln $AUC_{0-T}$ | 0.98 | >0.99 | 14.1 | [0.92; 1.04] |
| | Ln $AUC_{0-Inf}$ | 1.01 | >0.99 | 12.6 | [0.96; 1.07] |
| | Ln $C_{max}$ | 0.97 | >0.99 | 17.7 | [0.90; 1.05] |
| | $AUC_{0-T}$ (ng · h/ml) | 0.97 | >0.99 | 15.1 | [0.91; 1.03] |
| | $AUC_{0-Inf}$ (ng · h/ml) | 1.01 | >0.99 | 14.7 | [0.94; 1.07] |
| | $C_{max}$ (ng/ml) | 0.95 | 0.99 | 19.4 | [0.87; 1.02] |

It is to be understood that while the invention has been described above using specific embodiments, the description and examples are intended to illustrate the structural and functional principles of the present invention and are not intended to limit the scope of the invention. On the contrary, the present invention is intended to encompass all modifications, alterations, and substitutions.

What is claimed is:

1. A method of treating a hepatitis-C virus infection with ribavirin administered in combination with interferon alfa-2*a* or alfa-2*b* in a patient in need thereof, the ribavirin administration consisting of administering to the patient exactly one dosage form comprising 400 mg to 600 mg of ribavirin twice daily.

2. The method of claim 1, wherein the dosage form comprises 400 mg of ribavirin and further comprises at least one excipient selected from the group consisting of microcrystalline cellulose, lactose monohydrate, crosscarmellose sodium, povidone and magnesium stearate.

3. The method of claim 1, wherein the dosage form is a 400 mg tablet which has at least one of the following characteristics:
   a tablet hardness of from about 10.27 kp to about 12.88 kp;
   a tablet weight of from about 0.5470 g to about 0.5535 g;
   a tablet thickness of from about 4.86 mm to about 4.91 mm; and
   a tablet friability of from about 0.23% to about 0.26%.

4. The method of claim 1, wherein the dosage form comprises 600 mg of ribavirin and further comprises at least one excipient selected from the group consisting of microcrystalline cellulose, lactose monohydrate, crosscarmellose sodium, povidone and magnesium stearate.

5. The method of claim 1, wherein the dosage form is a 600 mg tablet which has at least one of the following characteristics:
   a tablet hardness of from about 10.64 kp to about 12.58 kp;
   a tablet weight of from about 0.8174 g to about 0.8357 g;
   a tablet thickness of from about 6.38 mm to about 6.41 mm; and
   a tablet friability of from about 0.23% to about 0.33%.

6. The method according to claim 1, wherein the dosage form is a tablet which is dispensed in HDPE bottles.

7. The method according to claim 1, wherein the dosage form is a tablet which is dispensed in a unit dose package.

8. The method according to claim 7, wherein the unit dose package is a blister pack.

9. In a method of treating a hepatitis-C virus infection in a patient in need thereof comprising administering to the patient interferon alfa-2*a* or alfa-2*b* and a daily divided dose of 4 to 6 dosage forms each containing 200 mg ribavirin, the improvement consisting of administering to the patient exactly one dosage form comprising 400 mg to 600 mg of ribavirin twice daily instead of the daily divided dose of 4 to 6 dosage forms each containing 200 mg ribavirin.

10. The method of claim 9, wherein the dosage form is a tablet which comprises 400 mg of ribavirin.

11. The method of claim 9, wherein the dosage form is a tablet which comprises 600 mg of ribavirin.

12. The method of claim 9, wherein the dosage form is a tablet which comprises 400 mg to 600 mg of ribavirin.

13. The method of claim 9, wherein the dosage form is a tablet which is dispensed in a unit dose package.

14. The method of claim 9, wherein the dosage form is a tablet which is dispensed in HDPE bottles.

15. The method of claim 1, wherein the dosage form is a tablet which comprises 400 mg of ribavirin.

16. The method of claim 1, wherein the dosage form is a tablet which comprises 600 mg of ribavirin.

17. The method of claim 1, wherein the dosage form is a tablet which comprises 400 mg to 600 mg of ribavirin.

* * * * *